United States Patent [19]

Arnold

[11] Patent Number: 5,759,570
[45] Date of Patent: Jun. 2, 1998

[54] MULTI-LAYER WOUND DRESSING

[75] Inventor: Peter Stuart Arnold, Skipton, United Kingdom

[73] Assignee: Johnson & Johnson Medical, Inc., Arlington, Tex.

[21] Appl. No.: 745,112

[22] Filed: Nov. 7, 1996

Related U.S. Application Data

[63] Continuation of Ser. No. 153,396, Nov. 16, 1993, abandoned.

[30] Foreign Application Priority Data

Nov. 23, 1992 [GB] United Kingdom ............... 9224592

[51] Int. Cl.⁶ .................................................. A61F 13/00
[52] U.S. Cl. .............. 424/443; 424/445; 604/304
[58] Field of Search .................... 424/493, 443, 424/445; 604/304

[56] References Cited

U.S. PATENT DOCUMENTS

| | | | |
|---|---|---|---|
| 3,888,247 | 6/1975 | Stenvall | 128/155 |
| 4,499,896 | 2/1985 | Heinecke | 128/156 |
| 4,532,937 | 8/1985 | Miller | 424/448 |
| 4,657,006 | 4/1987 | Rawlings et al. | 602/47 |
| 4,803,078 | 2/1989 | Sakai | 424/445 |
| 4,820,293 | 4/1989 | Kamme | 604/368 |
| 4,867,881 | 9/1989 | Kinzer | 210/490 |

FOREIGN PATENT DOCUMENTS

| | | |
|---|---|---|
| 0031018 | 7/1981 | European Pat. Off. |
| 0243179 | 10/1987 | European Pat. Off. |
| 0441417 | 8/1991 | European Pat. Off. |

OTHER PUBLICATIONS

Abstract of JP-A-60 072 557, originally published Apr. 1985.
Abstract of JP-A-59 051 849 originally published Mar. 1984.
Abstract of JP-A-04 282 152 originally published Oct. 1992.

*Primary Examiner*—D. Gabrielle Phelan
*Attorney, Agent, or Firm*—Andrew C. Farmer; James Riesenfeld

[57] ABSTRACT

The invention provides wound dressings comprising a molecular filtration membrane having a maximum pore size in the range of from 0.001 μm to 0.5 μm, and preferably in the range of from 0.01 μm to 0.25 μm. The wound dressings may also comprise an absorbent layer atop the molecular filtration membrane and/or a wound contact layer of wound-friendly bioabsorbable material for contacting the wound. In use, the molecular filtration membrane retains high molecular weight biopolymers and wound healing factors at the wound surface while excluding bacteria and allowing rapid egress of wound exudate through the membrane into the absorbent layer.

13 Claims, 1 Drawing Sheet

MULTI-LAYER WOUND DRESSING

This is a continuation of application Ser. No. 08/153,396, filed Nov. 16, 1993, now abandoned.

The present invention relates to multilayer wound dressings for the treatment of damaged, burned, ulcerated or otherwise traumatised mammalian skin.

The use of wound dressings to cover and protect wounds is very well known. Preferably, the wound dressing should provide a sterile environment at the wound site and should rapidly absorb wound exudate while maintaining a moist wound surface. The dressing should interfere as little as possible with wound healing and should be easy to remove and replace with minimal trauma. Finally, the wound dressing should be inexpensive to make, compact and conformable to all skin surfaces.

U.S. Pat. No. 4,499,896 (Steven B. Heinecke) discloses a multilayer reservoir wound dressing comprising an inner membrane of conformable, moisture vapour-permeable, liquid water-impermeable material having at least one hole therein through which exudate can pass, an intermediate absorbent layer, and an imperforate outer layer of a conformable, moisture vapour-permeable, liquid-impermeable material. The wound dressing is secured to the skin by an adhesive coating around the edges of the inner membrane. Wound exudate is absorbed through the holes in the inner membrane into the intermediate absorbent layer. From there water vapour escapes through the semipermeable outer membrane. The remainder of the wound exudate other than water is retained in the intermediate layer.

The reservoir wound dressing disclosed in U.S. Pat. No. 4,499,896 suffers from the disadvantage that tissue ingrowth into the holes in the inner membrane can give rise to major trauma when the dressing is removed.

EP-A-0441417 (The Kendall Company) discloses a conformable multilayer reservoir wound dressing similar to that described in U.S. Pat. No. 4,499,896, but having multiple perforations in the inner membrane and an air-permeable window in the outer protective membrane. This structure will suffer from the same drawback as enumerated above for the structure disclosed in U.S. Pat. No. 4,499,896.

U.S. Pat. No. 3,888,247 (Carl B. Stenvall) discloses a wound dressing comprising an inner microporous membrane, an intermediate absorbent layer and an outer, protective air-permeable tape. The inner microporous membrane is imperforate and is coated with pressure-sensitive adhesive over the whole of one side such that, in use, the entire surface of the inner microporous membrane is adhered to the wound site. The inner microporous membrane has pores ranging in diameter from 1 to 20 microns with an average pore size of 15 microns. The resulting wound dressing absorbs wound exudate through the pores of the microporous inner membrane and is said to provide improved wound healing and less scar formation than conventional wound dressings.

It has now been found that a novel wound dressing comprising a liquid-permeable molecular filtration membrane can provide all of the above-enumerated advantages of the prior art and can additionally provide an improved environment for wound healing.

The present invention provides a wound dressing comprising a molecular filtration membrane having a maximum pore size in the range of from 0.001 μm to 0.5 μm.

Preferably the maximum pore size is in the range of from 0.01 μm to 0.5 μm. More preferably the range is from 0.01 μm to 0.25 μm and most preferably the range is from 0.02 μm to 0.2 μm.

Here and elsewhere in the description the term "maximum pore size" refers to the pore size as determined by the Pall microbial challenge test. This test is based on measuring the filtration performance of the membrane when challenged with laboratory test microbes of varying dimensions. For example, if the membrane blocks the passage of *Serratia marcescens* the maximum pore size is 0.45 μm. If the membrane blocks the passage of *Pseudomonas diminuta* (ATCC 19146) then the maximum pore size is 0.2 μm, and so on. The test microbes include viruses such as murine leukaemia viruses (maximum pore size 0.08–0.12 μm) and *E. Coli* endotoxin molecules (maximum pore size 0.001 μm).

The term "maximum pore size" refers only to the intrinsic pores of the membrane material and obviously does not include macroscopic perforations in the membrane. In any case, the membrane will normally be imperforate.

The above-defined measurement of maximum pore size in the molecular filtration membrane is the most appropriate for biological applications such as the wound dressings of the present invention. Furthermore, it has also been found that there is good correlation between the maximum pore size as defined above and average pore sizes determined by physical methods such as gas permeability measurements or thermoporometry. Particularly good correlation is observed with average pore sizes determined by the Formal Flow Test (FFT) technique. In the FFT technique the flow of air through a wetted membrane is measured as a function of the pressure difference across the membrane. The pressure difference at which the rate of flow of air through the wetted membrane ceases to increase linearly with increasing pressure difference is known as the KL value, and shows a strong inverse correlation with the maximum pore size as defined above.

The maximum pore size as defined herein also correlates well with data from solute rejection experiments.

The molecular filtration membrane may for example comprise polysulphone, Nylon 66, cellulose, a cellulose derivative, polyvinylidene fluoride, polyurethane, PTFE, polylactic derivatives, polyglycolic derivatives, insoluble derivatives of naturally derived biopolymers and mixtures thereof. It will normally be imperforate, permeable to aqueous liquids and highly conformable to the wound surface.

The permeability to aqueous liquids of the molecular filtration membrane can be controlled by adjusting the porosity, hydrophobicity and charge of the membrane. Normally the molecular filtration membrane will be highly permeable to aqueous liquids so as to allow even a heavy flow of wound exudate to wick rapidly through the membrane. This contrasts with the semipermeable membranes of prior art dressings, which are impermeable to aqueous liquids. In the wound dressings according to the present invention high molecular weight components of wound exudate such as wound healing factors, plasma proteins and the like are unable to pass through the molecular filtration membrane and are retained at the wound site. Leucocytes and other cells cannot pass through the molecular filtration membrane and are retained at the wound site. Conversely, bacteria cannot pass through the molecular filtration membrane to infect the wound.

The multilayered wound dressing according to the present invention provides an improved wound healing environment at the wound site. It achieves this by retaining at the wound site those wound healing factors such as cytokines (e.g. TGFβ, FGFβ, EGF, PDGF, IL-1 and others), glycosaminoglycans and proteins that have molecular weights too high to enable them to pass through the molecular filtration membrane. Useful low molecular weight hormones such as TGFβ are retained at the wound site because they complex strongly with large molecular weight molecules such as glycosaminoglycans. At the same time, excess water and low molecular weight molecules from the wound exudate are swiftly removed through the molecular filtration membrane into the absorbent layer. The overall effect of the molecular filtration membrane is thus actually to increase the concentration at the wound site of the high molecular weight wound healing compounds above the concentration that occurs naturally in wound exudate. The absence of the higher molecular weight chemotactic factors from the absorbent layer helps to prevent tissue ingrowth into the absorbent layer, thereby reducing wound trauma when the dressing is removed. Furthermore, the wound dressing is particularly advantageous for use in conjunction with wound healing ointments or the like that contain high molecular weight wound healing factors, because the molecular filtration membrane prevents the wound healing factors being diluted and washed away into the absorbent layer by the flow of wound exudate.

In the wound dressing according to the present invention the molecular filtration membrane is attached to the body over a wound site. The means of attachment will normally be a pressure-sensitive adhesive bonded to skin around the wound site. Suitable adhesives include acrylic polymer adhesives well known in the wound dressing art, such as the copolymers of butyl acrylate and butyl methacrylate. The adhesive may be applied to the molecular filtration membrane as a layer extending around the perimeter of the membrane leaving the central part of the membrane free from adhesive. Alternatively, the adhesive may be provided on a second membrane such as a semipermeable membrane extending around and beyond the edge of the molecular filtration membrane and adhesively bonded to the molecular filtration membrane. The adhesive may extend over the whole of one side of the second membrane or only over a marginal portion of the second membrane. The quantity of adhesive employed will usually be from 20 g/m$^2$ to 50 g/m$^2$, and preferably from 35 g/m$^2$ to 45 g/m$^2$.

The wound dressing according to the present invention also comprises an absorbent layer atop the molecular filtration membrane to absorb wound exudate passing through the molecular filtration membrane. The absorbent layer is held in place by an outer protective membrane atop the absorbent layer. The outer protective membrane also prevents exudate absorbed in the absorbent layer from leaking out to stain clothes or bedclothes.

The outer protective membrane is preferably a semipermeable membrane, such as one of the semi-permeable polyurethane membranes widely used in the wound dressing art. In this context "semi-permeable" means that the membrane is permeable to water vapour and air but impermeable to aqueous liquids. Typically the water vapour permeability will be in the range of from 1000 g/m$^2$/24 hr to 3000 g/m$^2$/24 hr. Continuous polyurethane films having such properties are available under the Trade Mark PLATILON from Plate Bonn GmbH, Bonn, Germany. Such a membrane has extremely small pore size (typically less than 1 μm) and is therefore an effective bacterial barrier.

Preferably the outer protective membrane extends beyond the edges of the molecular filtration membrane and the absorbent layer and is provided with an adhesive coating as described above for attaching the multilayered wound dressing to the skin over the wound.

The absorbent layer is preferably completely enclosed between the inner molecular filtration membrane and the outer semi-permeable membrane. Accordingly, a wide range of absorbent materials such as fabrics, superabsorbents, foams or particulate absorbents may be used as or in the absorbent layer. The absorbent materials should be conformable and also should not react or hydrolyse in the presence of wound exudate to give low-molecular weight fragments that could diffuse back through the molecular filtration membrane and interfere with wound healing. The absorbency of the absorbent layer will normally be in the range of from 500 g/m$^2$ to 10,000 g/m$^2$. The absorbent layer contains active ingredients for treating the wound. They may include low molecular weight microbiocides such as chlorhexidine that can diffuse back through the molecular filtration membrane to maintain a steril environment in the wound. The active ingredients may also or alternatively include low-molecular weight active ingredients such as humectants (e.g. glycerol), oligosaccharides or oligopeptides that can be beneficial to wound healing, or materials pharmacologically active on wound healing such as pharmaceuticals and growth factors.

The multi-layered wound dressing according to the present invention further comprises a wound contact layer attached to the molecular filtration membrane and formed from a bioabsorbable material that forms a wound-friendly and bioabsorbable gel on contact with wound exudate.

Accordingly, the wound contact layer comprises a bioabsorbable and hydrophilic polymeric material. This may be one of the well known synthetic bioabsorbable polymers such as polyglycolic acid, polylactic acid or copolymers thereof, or the hydrogel matrix (preferably of K-Y™ hydrogel) disclosed in co-pending Patent application EP-A-0532275, polymer such as collagen, chitin, keratin, an alginate, guar gum, locust bean gum or derivatives or mixtures thereof. The layer also may comprise a bioabsorbable polymer formed by chemically modifying a natural substance, for example, oxidised cellulose or chitosan or a cross-linked hyaluronic acid gel such as the kind described in GB-B-2168067 (Biomatrix Inc.).

The wound contact layer preferably also comprises one or more compounds that are known to assist wound healing, such as cytokines, protease inhibitors or glycosaminoglycans. The preferred wound healing agents are the glycosaminoglycans, such as dermatan sulphate, chondroitin sulphate, heparin, heparan sulphate, hyaluronic acid or derivatives or mixtures thereof.

Additionally, the wound contact layer may contain antibodies directed against factors associated with wound healing or against receptors for these factors in order to modulate the levels of these factors (for example growth factors such as TGFβ1) and therefore alter wound healing rates and/or scar tissue formation.

Preferably the wound contact layer comprises collagen, either with or without the addition of a glycosaminoglycan, preferably chondroitin sulphate. The wound contact layer may also comprise a humectant such as a polyhydric alcohol and/or an antiseptic such as chlorhexidine, and/or an antibiotic.

The wound contact layer absorbs wound exudate and provides a biocompatible wound-friendly environment. Preferably, the wound contact layer absorbs wound exudate to form a bioabsorbable gel, thereby reducing the risk that liquid exudate will leak out of the dressing and soil clothes or bedclothes. The layer of wound-friendly gel prevents the wound contact part of the dressing from adhering to the wound, and so makes removing and replacing the wound dressing very easy and non-traumatic. Even more importantly, a bioabsorbable gel layer can function as a slow release matrix for wound healing substances such as glycosaminoglycans, protease inhibitors, added cytokines/ growth factors, antibodies or other pharmacological modulators of wound healing. Likewise, the same layer can function as a slow release matrix for antiseptics or antibiotics.

Furthermore, many gel-forming bioabsorbable biopolymers are themselves known to assist wound healing. They include glycosaminoglycans, collagen, chitin and the alginates. Such substances are preferred constituents of the wound contact layer. They are preferred on account of their abundance, availability from natural sources, low cost and well-understood properties. Biopolymer-containing films can be made with controlled bioabsorption rates. For example, heating or glycosylating collagen will speed up the rate at which it is bioabsorbed, whereas cross-linking collagen will reduce the rate of bioabsorption. In this way the rate at which the wound contact layer delivers active agents to the wound can be optimised.

Wound healing compositions comprising a collagen matrix containing a glycosaminoglycan wound healing agent are disclosed, for example, in EP-A-0251695 and EP-A-0314109 (both to University of Medicine and Dentistry of New Jersey).

The bioabsorbable gel wound healing compositions are especially advantageous when used in conjunction with wound dressings according to the present invention because the molecular filtration membrane of the wound dressing holds the gel in contact with the wound without allowing any of the high molecular-weight gel to pass through into the absorbent layer of the dressing. At the same time, excess liquid exudate from the wound can pass rapidly through the molecular filtration membrane to be absorbed by the intermediate absorbent layer. Conversely, low molecular weight active compounds from the absorbent layer can flow back through the molecular filtration membrane and diffuse into the gel wound contact layer. Finally, the wound dressing maintains a sterile environment in the wound contact layer.

The wound contact layer may be integral with the rest of the multilayered wound dressing. For example, it may be formed by depositing a mixture of the constituents in solution, dried or gel form on the wound contacting surface of the molecular filtration membrane followed by evaporating the solvent to leave a dried film that swells to form the wound contact layer when it absorbs liquid wound exudate. The weight per unit area of the dried film is preferably in the range from 30 g/m² to 600 g/m², and more preferably from 70 g/m² to 210 g/m².

Alternatively, the wound contact layer may be applied to the wound separately as an ointment, dressing powder or film, prior to applying a wound dressing according to the present invention.

An embodiment of the present invention will now be described in detail, by way of example, with reference to the accompanying drawing. The drawing shows a cross-section through a multilayered wound dressing according to the present invention.

BRIEF DESCRIPTION OF THE DRAWING

The multilayered wound dressing 1 comprises an outer protective membrane 2, an intermediate absorbent layer 3, a molecular filtration membrane 4 and a wound contact layer 5. The wound dressing further comprises a layer of pressure-sensitive adhesive 6 and a release-coated protective film 7.

The outer protective membrane 2 is an imperforate semi-permeable membrane formed from the semi-permeable polyurethane film sold under the Trade Mark PLATILON by Plate GmbH, Bonn, Germany, and well known in the wound dressing art. The membrane is impermeable to liquids but permeable to water vapour.

Figure 1:
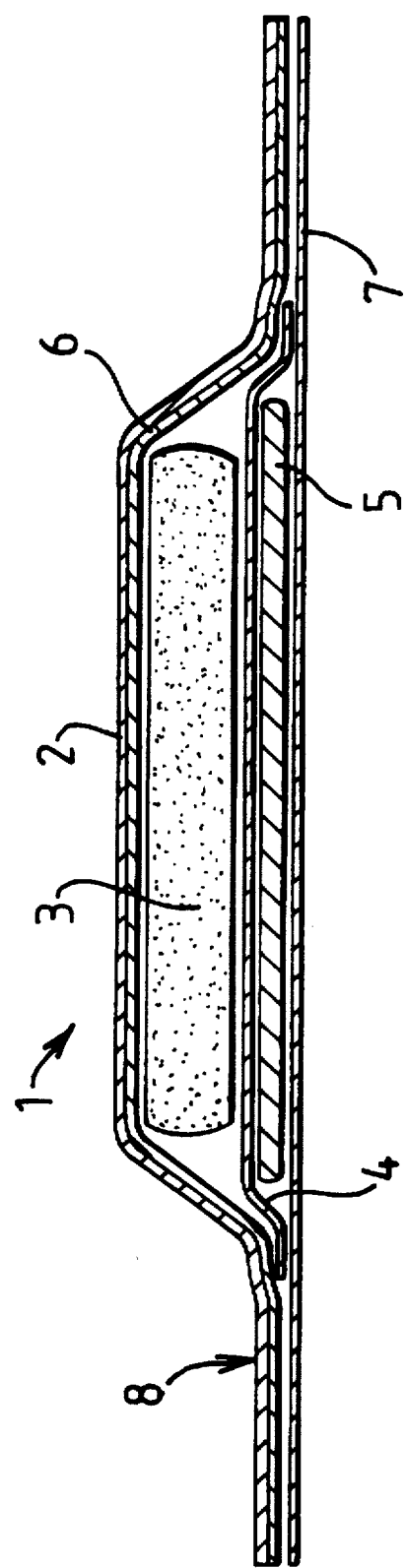

The outer protective membrane 2 extends beyond the edges of the other layers 3, 4, 5 of the wound dressing to form a marginal portion 8. The outer protective membrane 2 is coated on one side with pressure-sensitive adhesive 6. The adhesive extends onto the marginal portion 8, where it is used for attaching the wound dressing to the skin of the patient. Depending on the overall dimensions of the wound dressing the adhesive-coated marginal portion will be from 10 to 20 mm wide. The molecular filtration membrane and the adhesive-coated marginal portion form an effective bacterial seal over the wound.

The intermediate absorbent layer 3 consists of a layer of the absorbent material sold under the Registered Trade Mark TOPPER and a layer of polyurethane foam. The pad is held in place by the adhesive layer 6.

The molecular filtration membrane 4 is a microporous hydrophilic ultrafiltration membrane made of polyvinylidene fluoride and available under the Trade Mark "Emflon II" from Pall Corporation, East Hills, N.Y. 11544, U.S.A. The membrane has a maximum pore size of 0.2 μm as determined by the Pall microbial challenge test. That is to say, the membrane excludes the bacterium *Pseudomonas diminuta* (ATCC 19146), which has a nominal size of 0.2 μm, but allows *Acholeplasma Laidlawii* with a nominal size of 0.1 μm to pass through.

The effective molecular weight filtration limit of the molecular filtration membrane under wound healing conditions can be determined by means of a solute rejection experiment as follows. A multilayered wound dressing of the kind described herein is immersed in plasma containing defined amount of radioactively labelled protein, glycosaminoglycan or complex having a defined molecular weight. The wound dressing and plasma are incubated at 37° C. for 24 hours. The dressing is then removed and dissected into its individual components for determination of radioactive content. Examination of the radioactive content of the absorbent layer shows whether protein of the defined molecular weight has been absorbed through the molecular weight filtration membrane, and examination of the molecular weight filtration membrane itself shows the level of adsorption by this membrane. The adsorption result gives an indication of adherence. The molecular weight filtration limit is defined as that molecular weight which is 90% rejected by the molecular filtration membrane.

The molecular filtration membrane 4 extends beyond the edge of the absorbent layer, and the periphery of the molecular filtration layer is adhered to the outer protective membrane 2 by the adhesive layer 6. In this way the absorbent layer 3 is entirely enclosed by the membranes 2 and 4 thereby preventing any leakage of fluid absorbed in the absorbent layer.

The molecular filtration membrane 4 is hydrophilic to assist wicking of exudate through the membrane. The porosity of the membrane is selected to provide both the requisite molecular weight filtration limit and high permeability to aqueous liquids.

The wound contact layer 5 is a layer of dried collagen/ glycosaminoglycan/glycerol that forms a wound-friendly bioabsorbable gel in contact with wound exudate. The glycosaminoglycan is chondroitin sulphate and the ratio of chondroitin sulphate:collagen:glycerol is 9:9:2 by weight. This base formulation can be used as a carrier for further active ingredients such as growth factors.

The above wound contact layer composition is prepared as a mixed aqueous solution, coated onto the molecular filtration membrane 4 and dried in air at 70° C. for 3 hours to form a clear transparent film. The weight per unit area of the dried film is approximately 150 g/m².

The wound contact layer 5 and the exposed part of the adhesive layer 6 are protected prior to use by a release-coated protective membrane 7. The protective membrane is formed from paper release-coated with a silicone.

The multilayered wound dressing is packaged in a hermetically sealed envelope and sterilised by gamma-irradiation, autoclaving or other suitable methods. Alternatively, the sterilisation may be carried out before the packaging step. In either case, a sterile wound dressing is produced.

The resulting wound dressing is conformable, absorbent and easy to replace with minimal wound trauma. The wound dressing provides a layer of wound-friendly bioabsorbable gel in contact with the wound. The molecular filtration membrane rapidly removes liquid wound exudate into the absorbent layer while preventing passage of natural wound healing factors or the high molecular-weight components of the wound contact layer. The smooth surface and small pore size of the molecular weight filtration membrane prevent ingrowth of cells so that trauma upon removal of the dressing is minimised. The wound dressing retains liquid wound exudate hygienically in the enclosed absorbent layer. Finally, the dressing acts as an effective bacterial barrier.

A number of possible modifications of the multilayered wound dressings according to the present invention have been indicated above. Additional modifications will be apparent to persons skilled in the art without departing from the scope of the present invention.

I claim:

1. A wound dressing comprising:

a wound contacting layer comprising a bioabsorbable and hydrophilic polymeric material that forms a gel in contact with wound exudate.

a liquid permeable molecular filtration membrane, having a maximum pore size in the range of from 0.001 µm to 0.5 µm;

an absorbent layer overlying the molecular filtration membrane and comprising a pharmaceutical, a wound healing agent, a growth factor or a microbiocide capable of passing through the molecular filtration membrane; and an outer protective membrane overlying the absorbent layer on the side opposite from the molecular filtration membrane.

2. The wound dressing of claim 1, wherein the molecular filtration membrane has a maximum pore size in the range of from 0.01 µm to 0.5 µm.

3. The wound dressing of claim 1, wherein the molecular filtration membrane has a maximum pore size in the range of from 0.01 µm to 0.25 µm.

4. The wound dressing of claim 1, wherein the molecular filtration membrane has a pore size in the range of from 0.02 µm to 0.2 µm.

5. The wound dressing of claim 1, wherein the molecular filtration membrane is selected from the group consisting of polysulfone, Nylon 66, cellulose, a cellulosic compound, polyvinylidene fluoride, polyurethane, PTFE, polylactic acid, polyglycolic acid, or copolymers thereof and mixtures thereof.

6. The wound dressing of claim 1 wherein the outer protective membrane is semipermeable.

7. The wound dressing of claim 1 wherein the outer protective membrane extends beyond the molecular filtration membrane and the intermediate absorbent layer, and is provided with an adhesive coating for attaching the wound dressing to mammalian skin in the vicinity of a wound.

8. The wound dressing of claim 1 wherein the biocompatible wound contact material is selected from the group consisting of collagen, chitin, fibrin, laminin, fibronectin, an alginate, a glycosaminoglycan, and mixtures thereof.

9. The wound dressing of claim 1 wherein the biocompatible wound contact material comprises a polyhydric alcohol.

10. The wound dressing of claim 1 wherein the biocompatible wound contact material comprises collagen and a glycosaminoglycan.

11. The wound dressing of claim 1 which is sterile.

12. The wound dressing of claim 1 wherein a marginal portion of the wound dressing membrane is coated with an adhesive layer for attaching the wound dressing to mammalian skin.

13. The wound dressing of claim 12 further comprising a release-coated protective membrane to protect said adhesive layer prior to using the wound dressing.

* * * * *